(12) United States Patent
Yang et al.

(10) Patent No.: US 10,150,950 B2
(45) Date of Patent: Dec. 11, 2018

(54) METHOD FOR CULTURING MESENCHYMAL STEM CELLS ACCORDING TO CELL SIZE

(71) Applicant: MEDIPOST CO., LTD., Seongnam-si, Gyeonggi-do (KR)

(72) Inventors: Yoon-Sun Yang, Seongnam-si (KR); Won Il Oh, Seongnam-si (KR); Hye Jin Jin, Seongnam-si (KR); Soon-Jae Kwon, Seongnam-si (KR); Miyeon Kim, Seongnam-si (KR)

(73) Assignee: MEDIPOST CO., LTD, Seongnam-si (KR)

( * ) Notice: Subject to any disclaimer, the term of this patent is extended or adjusted under 35 U.S.C. 154(b) by 87 days.

(21) Appl. No.: 14/915,680

(22) PCT Filed: Aug. 29, 2014

(86) PCT No.: PCT/KR2014/008079
§ 371 (c)(1),
(2) Date: Mar. 1, 2016

(87) PCT Pub. No.: WO2015/034212
PCT Pub. Date: Mar. 12, 2015

(65) Prior Publication Data
US 2016/0222353 A1 Aug. 4, 2016

(30) Foreign Application Priority Data
Sep. 5, 2013 (KR) .................. 10-2013-0106673

(51) Int. Cl.
*A61K 35/28* (2015.01)
*C12N 5/0775* (2010.01)

(52) U.S. Cl.
CPC ............ *C12N 5/0665* (2013.01); *A61K 35/28* (2013.01); *C12N 2500/02* (2013.01); *C12N 2500/14* (2013.01); *C12N 2500/16* (2013.01)

(58) Field of Classification Search
None
See application file for complete search history.

(56) References Cited

U.S. PATENT DOCUMENTS

| | | | |
|---|---|---|---|
| 5,486,359 A * | 1/1996 | Caplan | A61F 2/28 424/93.7 |
| 7,615,374 B2 * | 11/2009 | Vodyanyk | C12N 5/0662 435/325 |
| 2005/0265980 A1* | 12/2005 | Chen | C12N 5/0647 424/93.7 |
| 2009/0081784 A1* | 3/2009 | Vodyanyk | C12N 5/0662 435/372 |
| 2010/0015710 A1* | 1/2010 | Jung | C12N 5/0667 435/377 |
| 2010/0330047 A1 | 12/2010 | Valorani | |

FOREIGN PATENT DOCUMENTS

| | | |
|---|---|---|
| KR | 10-1138091 B1 | 4/2012 |
| KR | 10-2013-0013435 A | 2/2013 |
| WO | 2013121426 A1 | 8/2013 |
| WO | 2014046417 A1 | 3/2014 |

OTHER PUBLICATIONS

Japanese Patent Office; Communication dated Mar. 14, 2017 in corresponding Japanese Patent Application No. 2016-540796.
Li, Peng et al., "Role of hypoxia in viability and endothelial differentiation potential of UC-MSCs and VEGF interference," J.CentSouth Univ(Med Sci), vol. 38, No. 4, p. 329-340, 2013, (12 pages total).
Lavrentieva, Antonina et al., "Effects of hypoxic culture conditions on umbilical cord-derived human mesenchymal stem cells," Cell Communication and Signaling, vol. 8, No. 18; p. 1-9, 2010, (10 pages total).
European Patent Office; Communication dated Dec. 20, 2016, in counterpart European Application No. 14842224.9.
Ingrida Majore et al. "Identification of subpopulations in mesenchymal stem cell-like cultures from human umbilical cord" Cell Communication and Signaling, vol. 7, No. 1; Mar. 20, 2009 (8 pages total).
Chih-Chien Tsai et al. "Benefits of hypoxic culture on bone marrow multipotent stromal cells" Am J. Blood res. 2012; 2(3): (12 pages total).
Ruud Das, M.Sc. et al. "The Role of Hypoxia in Bone Marrow-Derived Mesenchymal Stem Cells: Considerations for Regenerative Medicine Approaches" Tissue Engineering: Part B, vol. 16, No. 2, 2010 (10 pages total).
Leticia Basciano et al., "Long term culture of mesenchymal stem cells in hypoxia promotes a genetic program maintaining their undifferentiated and multipotent status," BMC Cell Biology, Mar. 30, 2011, pp. 1-12; vol. 12, No. 12.
B. Corradetti et al., "Size-sieved subpopulations of mesenchymal stem cells from intervascular and perivascular equine umbilical cord matrix," Cell Proliferation, Aug. 2011, pp. 330-342, vol. 44.
Shih-Chieh Hung et al., "Isolation and Characterization of Size-Sieved Stem Cells from Human Bone Marrow," Stem Cells, 2002, pp. 249-258, vol. 20.
International Searching Authority, International Search Report of PCT/KR2014/008079 dated Dec. 8, 2014.

* cited by examiner

*Primary Examiner* — Blaine Lankford
(74) *Attorney, Agent, or Firm* — Sughrue Mion, PLLC

(57) ABSTRACT

A method for culturing mesenchymal stem cells. The method includes isolating mesenchymal stem cells having a size of 8 μm or less and culturing the mesenchymal stem cells in a medium containing calcium and magnesium and under a low oxygen condition. The method can significantly improve the proliferative capacity and differentiation potential of the mesenchymal stem cells.

11 Claims, 16 Drawing Sheets

METHOD FOR CULTURING MESENCHYMAL STEM CELLS ACCORDING TO CELL SIZE

CROSS REFERENCE TO RELATED APPLICATIONS

This is a National Stage of International Application No. PCT/KR2014/008079 filed Aug. 29, 2014, claiming priority based on Korean Patent Application No. 10-2013-0106673 filed Sep. 5, 2013, the contents of all of which are incorporated herein by reference in their entirety.

FIELD OF THE INVENTION

The present invention relates to a method for culturing mesenchymal stem cells according to cell size. More particularly, it relates to a method for isolating mesenchymal stem cells having a size of 8 μm or less, and culturing them under particular conditions.

BACKGROUND OF THE INVENTION

A "stem cell" is a generic name for an undifferentiated type of body cell found in tissues of embryos, fetuses and adults, which has the potential of differentiating into a diverse range of specialized cell types.

Stem cells can be classified depending on their potency: pluripotent stem cells, multipotent stem cells and unipotent stem cells. Pluripotent stem cells have pluripotency to differentiate into any type of cells. Embryonic stem cells and induced pluripotent stem (iPS) cells are representative of pluripotent stem cells. Adult stem cells show multipotency and/or unipotency. Among them are hematopoietic stem cells, mesenchymal stem cells, neural stem cells, etc.

In spite of various attempts to utilize the pluripotent human embryonic stem cells in cell therapeutics, the high likelihood of oncogenesis and immune rejection response still remain and are difficult obstacles to overcome.

In case of iPS cells, which are a type of stem cells purposely regressed from fully differentiated adult cells to their initial stage of embryonic stem cell stage by reprogramming, the risk of immune rejection response could be ruled out because they are autologous cells, but the risk of oncogenesis is still a problem to be solved.

As an alternative to solve these problems, mesenchymal stem cells have been suggested because they exhibit immunomodulatory effects and present no risk of oncogenesis. Mesenchymal stem cells are multipotent stem cells that can differentiate into a variety of cell types, including adipocytes, osteoblasts, chondrocytes, myoblasts, neuroblasts, myocardioblasts, hepatocytes, islet beta cells, vascular cells, etc., and are known to have the function of modulating immune responses.

Mesenchymal stem cells may be isolated from various tissues such as bone marrow, umbilical cord blood, adipose tissue, etc., but may not be sufficiently defined because cell surface markers are somewhat different from one another according to the origin from which the mesenchymal stem cells are derived. Generally, if they can differentiate into osteoblasts, chondrocytes and myoblasts, have a spindle shaped morphology, and express the surface markers CD73(+), CD105(+), CD34(−) and CD45(−), such stem cells are defined as mesenchymal stem cells. In this context, mesenchymal stem cells of different genetic origins and/or backgrounds do not significantly differ from one another under the standard definition, but are significantly different from one another in terms of in vivo activity. Further, when mesenchymal stem cells are used as an exogenous cell therapeutic agent, a limited pool of mesenchymal stem cells does not allow other available options, even in spite of low in vivo activity.

In addition, in order to apply the mesenchymal stem cells to clinical practice, it is essential to obtain a large amount of cells in initial stages and to culture them with passages, considering limited quantity of the mesenchymal stem cells which can be obtained from tissues. However, the mesenchymal stem cells form a very heterogeneous group during passages, which affects proliferation, differentiation, and aging of the cells, rendering the mesenchymal stem cells difficult to be developed as therapeutic agents.

In an effort to overcome these problems, Li J et al., Cell Research, 2008; Majore I et al., Cell Communication and Signaling, 2009; Rataiczak M Z et al., Aging, 2012, etc. disclose a variety of methods for culturing mesenchymal stem cells. However, these methods have several disadvantages: heterogeneous cells are obtained by the methods, making it difficult to obtain necessary number of cells for mass production, and the proliferative capacity of the cells decreases after each passage and aging of the cells progresses rapidly. Further, the equipment used in the above articles was not suitable for good manufacturing process (GMP), making its application to actual manufacturing process difficult. As such, there is a need for a method of extracting homogeneous group of cells and mass proliferating them efficiently and with low cost.

SUMMARY OF THE INVENTION

It is therefore an object of the present invention to provide a method for culturing mesenchymal stem cells efficiently.

It is another object of the present invention to provide mesenchymal stem cells prepared using the above method, which are improved in proliferative capacity and differentiation potential.

It is a further object of the present invention to provide a cell therapeutic agent comprising the mesenchymal stem cells.

In accordance with one aspect of the present invention, there is provided a method for culturing mesenchymal stem cells, comprising the steps of: (1) isolating mesenchymal stem cells having a size of 8 μm or less; and (2) culturing the mesenchymal stem cells in a medium containing 2.1 to 3.8 mM of calcium and 1.0 to 3.0 mM of magnesium under a condition of 2 to 5% oxygen.

In accordance with another aspect of the present invention, there is provided mesenchymal stem cells prepared by the above method, which are improved in proliferative capacity and differentiation potential.

In accordance with a further aspect of the present invention, there is provided a cell therapeutic agent comprising the mesenchymal stem cells.

A method of the present invention can significantly improve the proliferative capacity and differentiation potential of mesenchymal stem cells by isolating the mesenchymal stem cells having a size of 8 μm or less and culturing them in the presence of calcium, magnesium, and under a hypoxic (low oxygen) condition, allowing the mesenchymal stem cells obtained to be utilized as a cell therapeutic agent.

and in the form of single cells after trypsin treatment. Also shown is a graph illustrating a size distribution of the cells measured by Cellometer (FIG. 1c).

Figure 2A:
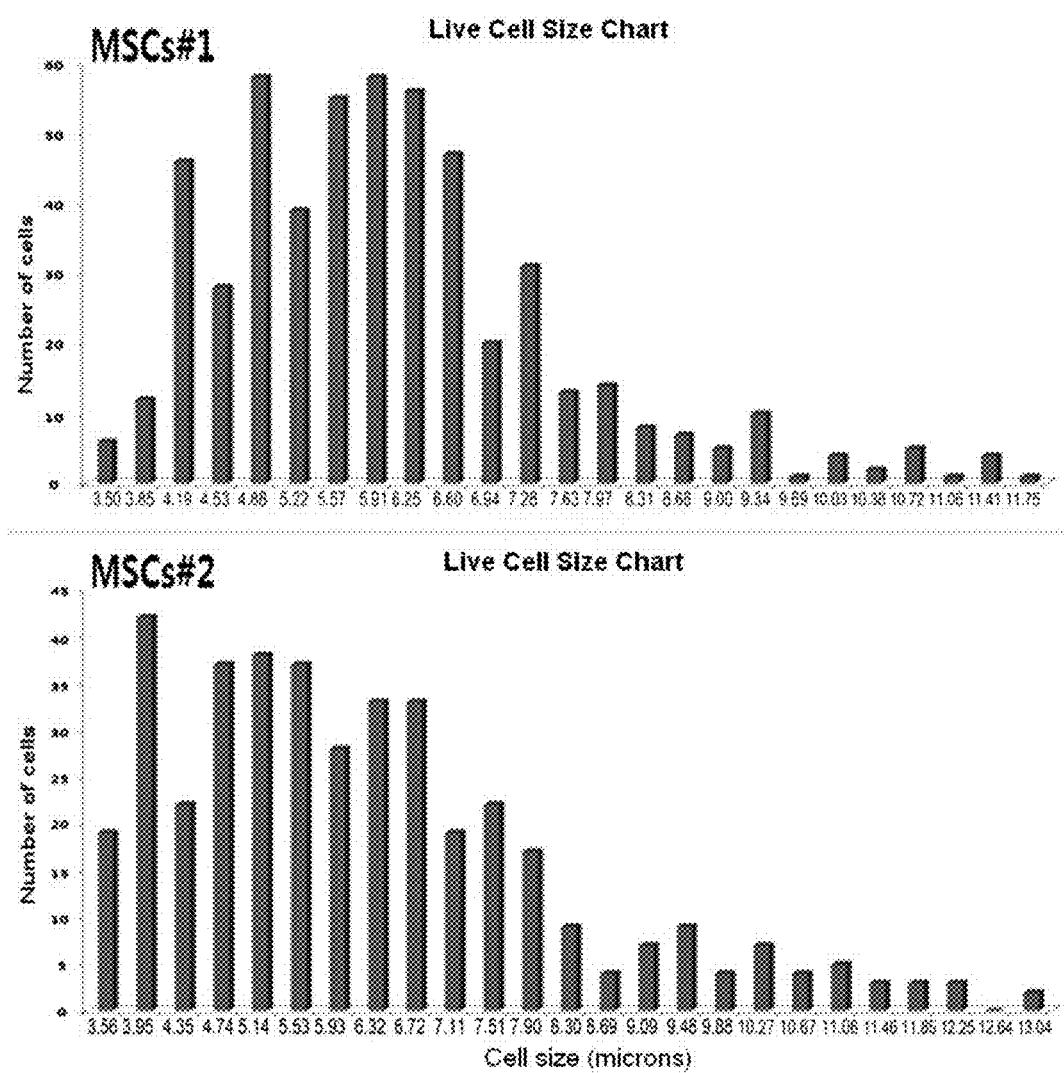
Figure 2B:
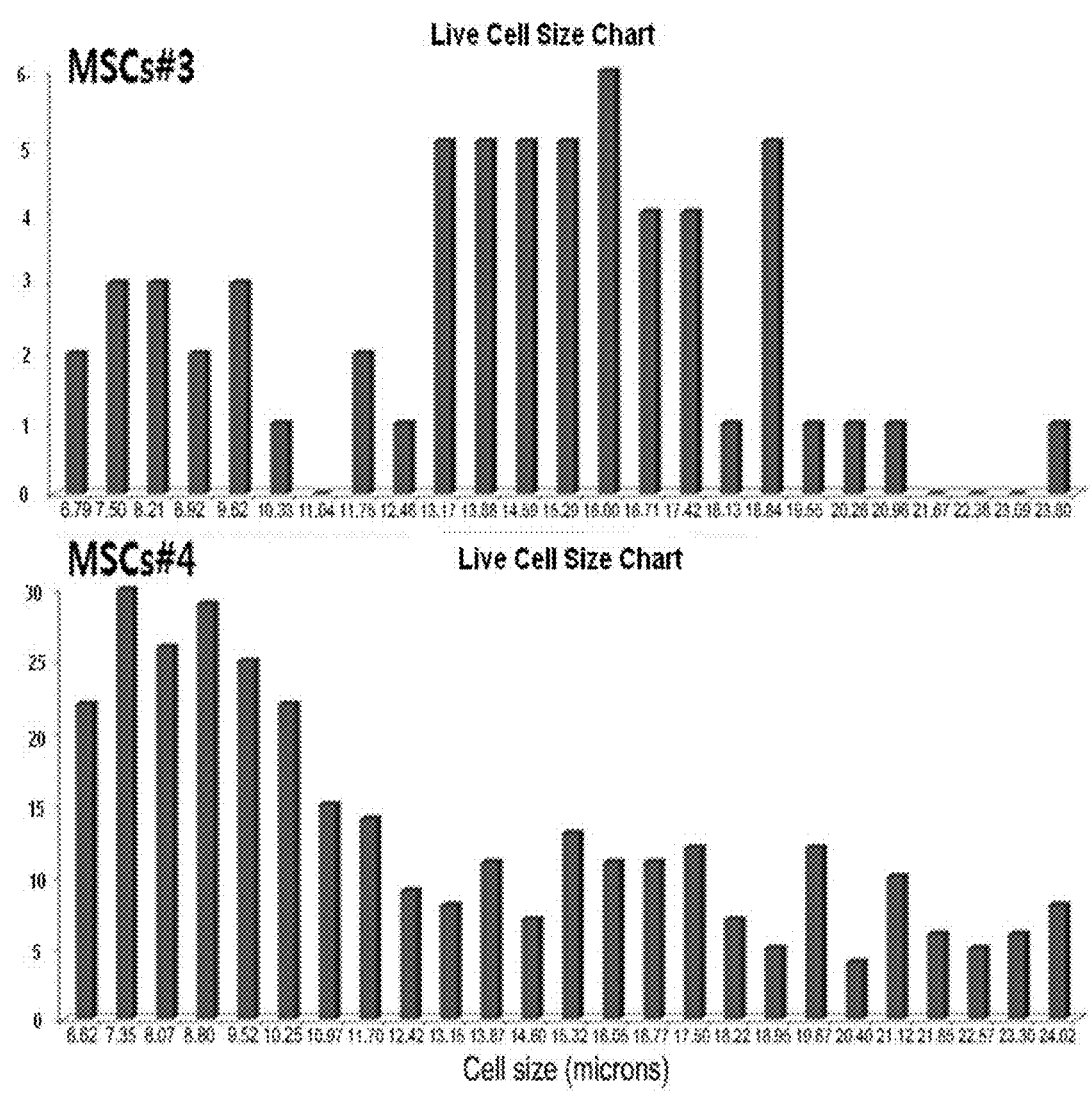

FIGS. 2A and 2B are graphs showing size distributions of cells measured by Cellometer, after culturing mesenchymal stem cells (MSCs #1 to #4).

Figure 3:
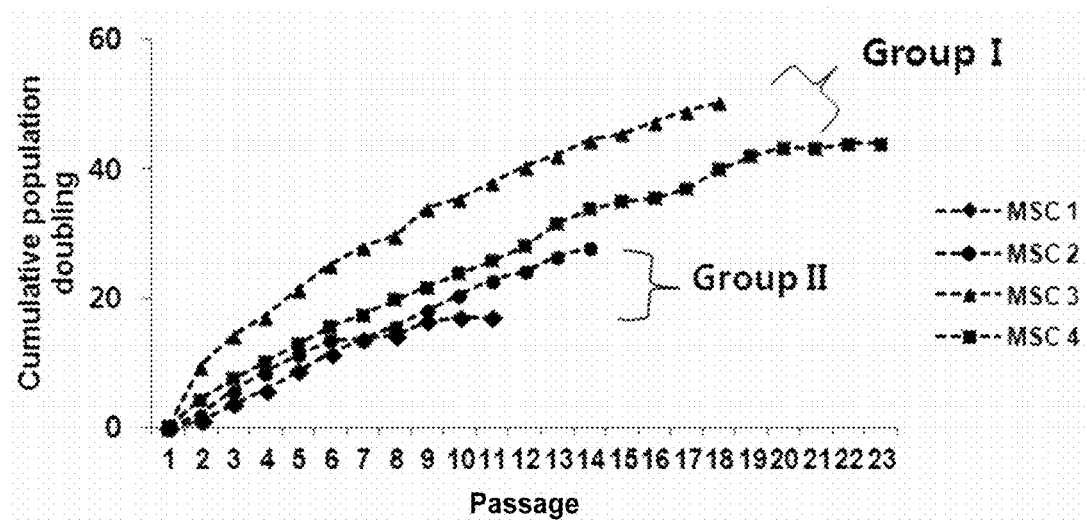

FIG. 3 is a graph showing cumulative population doubling (CPD) of a cell group I having a small size (MSCs #1 and #2), and a cell group II having a large cell size (MSCs #3 and #4), after culturing the cells with passages.

Figure 4:
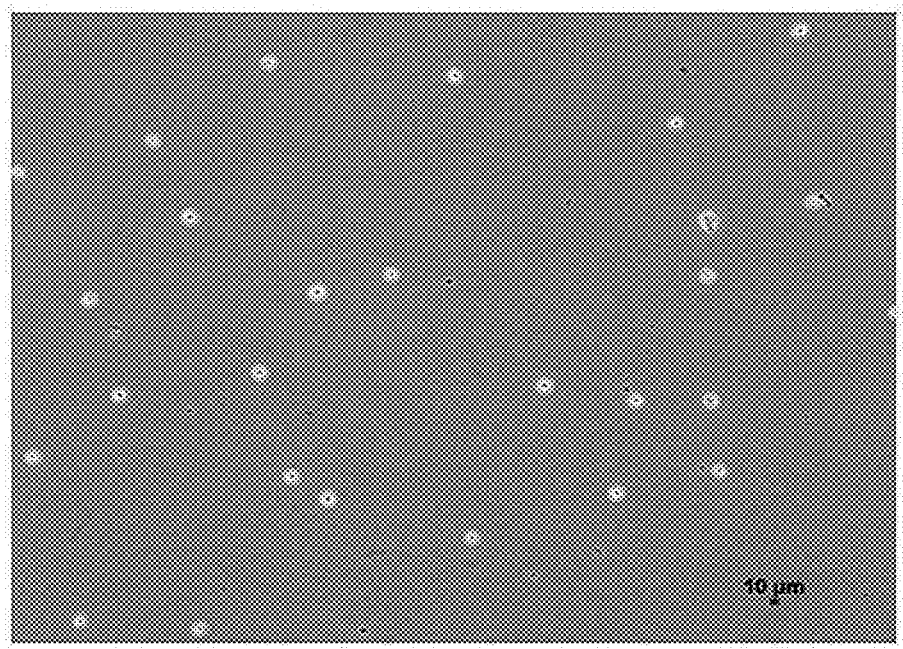

FIG. 4 is a microscopic photograph of mesenchymal stem cells having a size of 8 μm or less (small) obtained according to a method of the present invention.

FIG. 5a provides microscopic photographs of non-isolated cell group (original, left), a cell group with a cell size exceeding 8 μm (large, middle), and a cell group with a cell size of 8 μm or less (small, right). FIGS. 5b and 5c are graphs showing proliferation capacity and cumulative population doubling (CPD) of the three groups, respectively.

Figure 6:
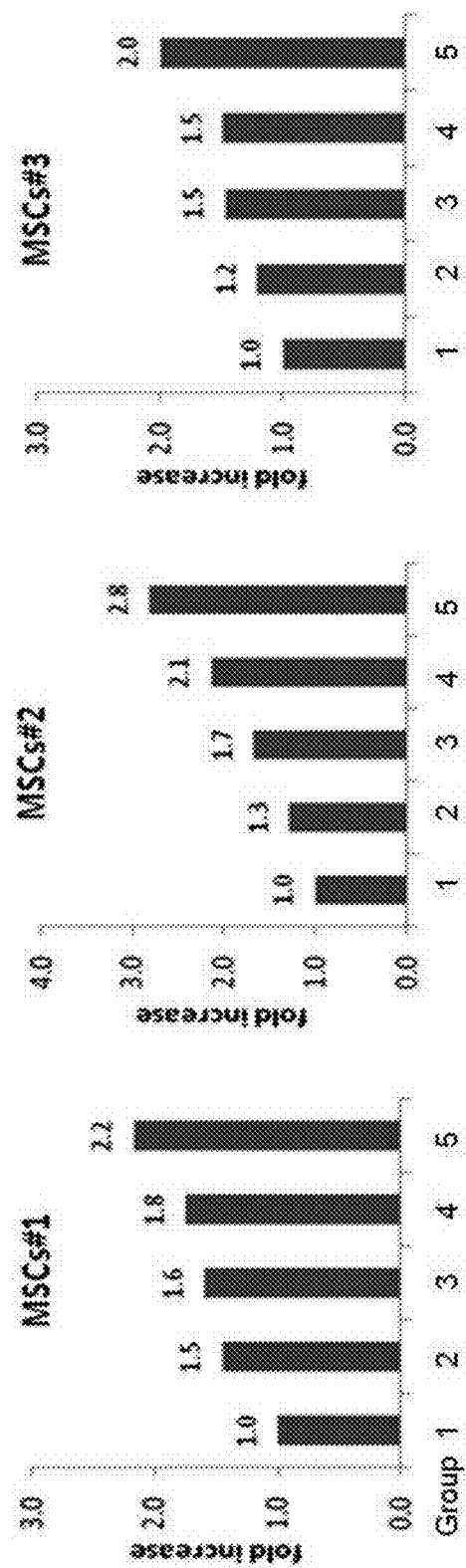

FIG. 6 are graphs showing proliferative capacity according to the ratio of mesenchymal cells having a size of 8 μm or less. Groups 1 to 5 in the graphs refer to mesenchymal stem cells (MSCs) composed of: MSCs exceeding 8 μm (100%); MSCs exceeding 8 μm (75%)+MSCs of 8 μm or less (25%); MSCs exceeding 8 μm (50%)+MSCs of 8 μm or less (50%); MSCs exceeding 8 μm (25%)+MSCs of 8 μm or less (75%); and MSCs of 8 μm or less (100%), respectively. The proliferative capacity of each group is presented as a fold increase compared to Group 1.

Figure 7:
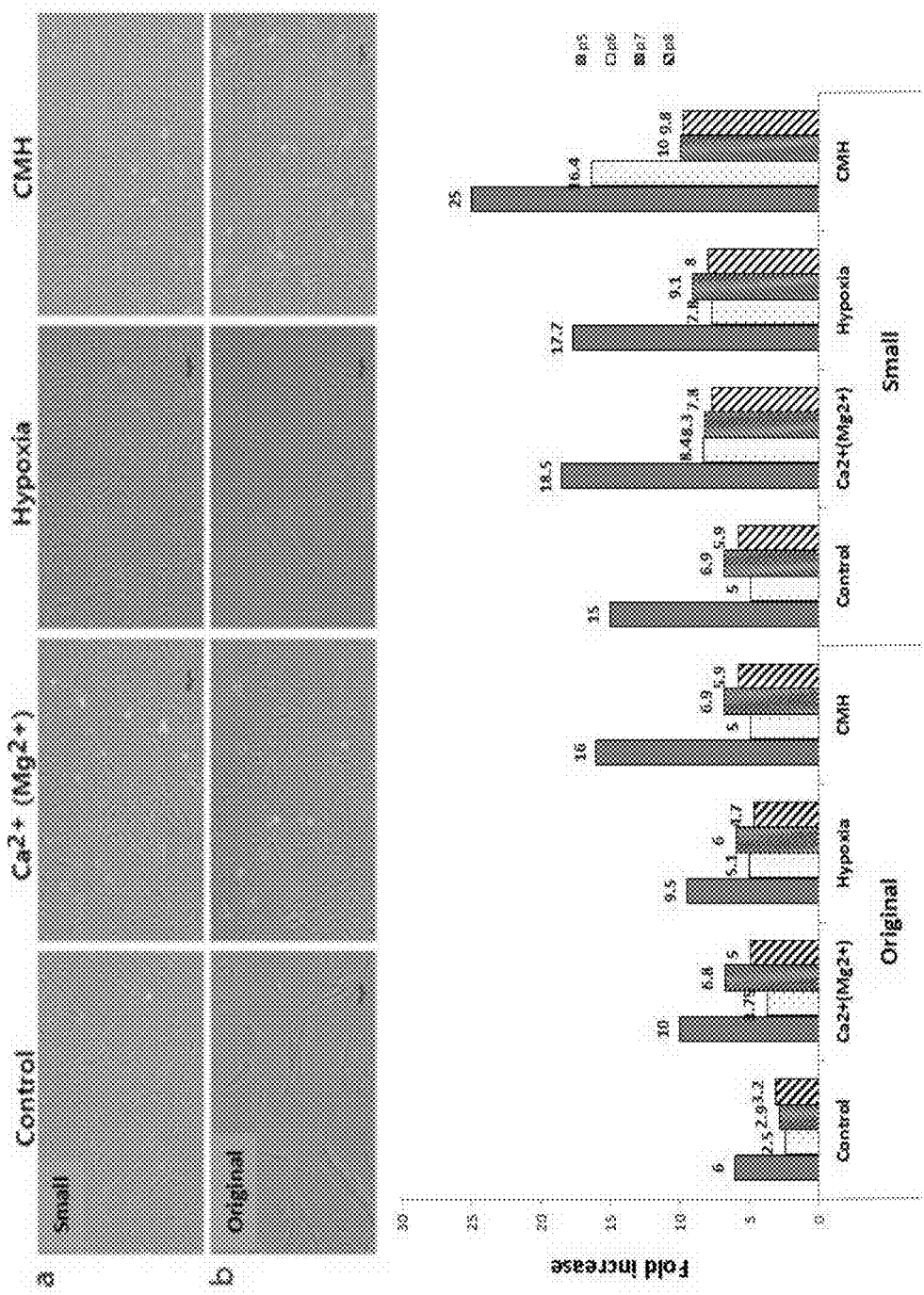

FIG. 7 shows results of examination of cell shape (a, b) and proliferation capacity of the cells (c), after culturing a cell group with a size of 8 μm or less (small) and non-isolated cell group (original), under a conventional culture condition (control), additional calcium (including magnesium) condition ($Ca^{2+}$ ($Mg^{2+}$)), hypoxic condition (hypoxia), and additional calcium (including magnesium) condition/hypoxic condition (CMH).

FIG. 8 provides graphs showing results of measuring the proliferation capacity (8A) and cumulative population doubling (8B), after culturing non-isolated cell group (original) and small cell group of 4 types of mesenchymal stem cells derived from umbilical cord blood (MSCs #1 to #4) with passages under a conventional culture condition and a CMH condition.

Figure 9:
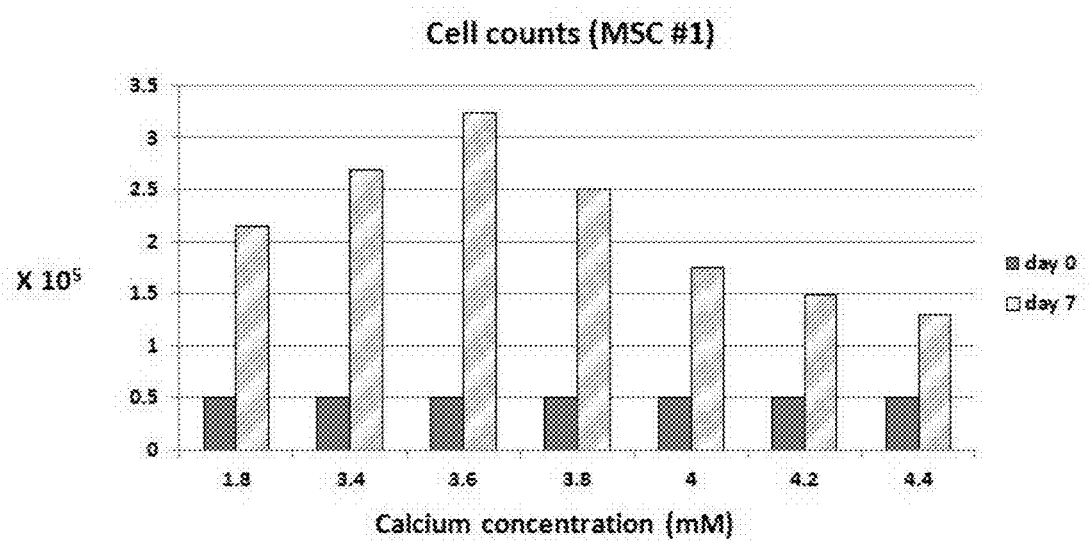

FIG. 9 is the result of cell counts after culturing one type of umbilical cord blood-derived mesenchymal stem cells (MSC #1) in the media containing calcium at the concentration of 1.8 to 4.4 mM for 6 days.

Figure 10:
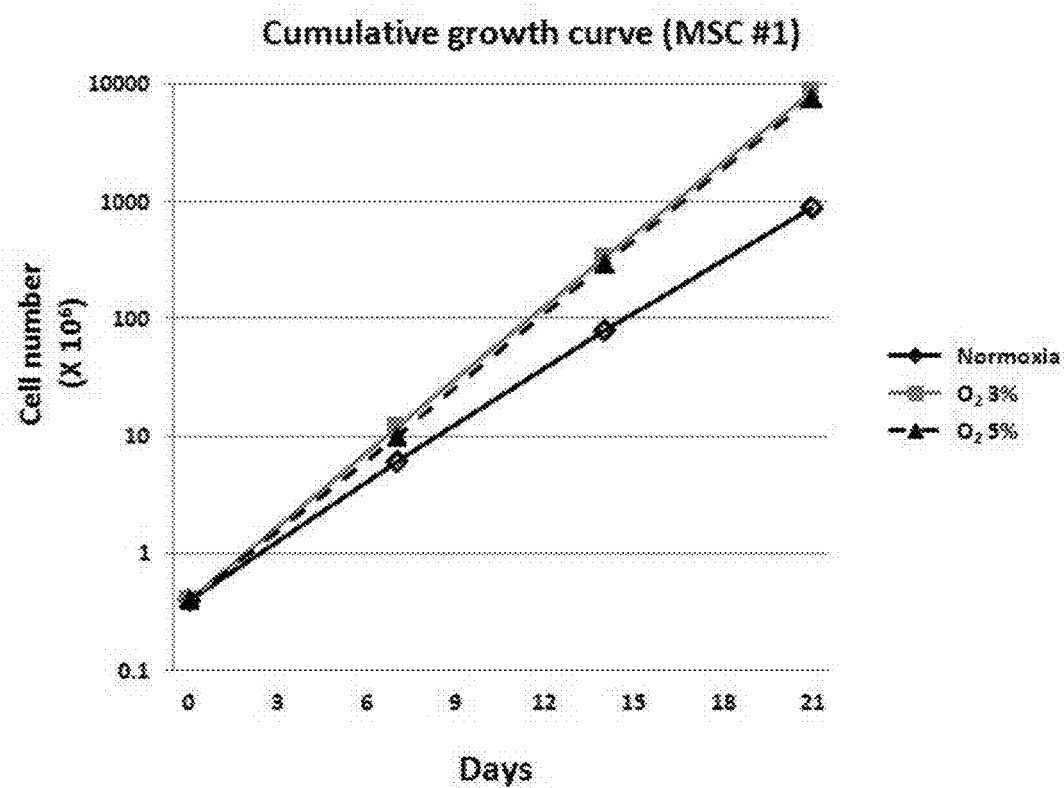

FIG. 10 is the result of cell counts after culturing one type of umbilical cord blood-derived mesenchymal stem cells (MSC #1) under the conditions of normal oxygen (normoxia), and 3% and 5% oxygen.

Figure 11:
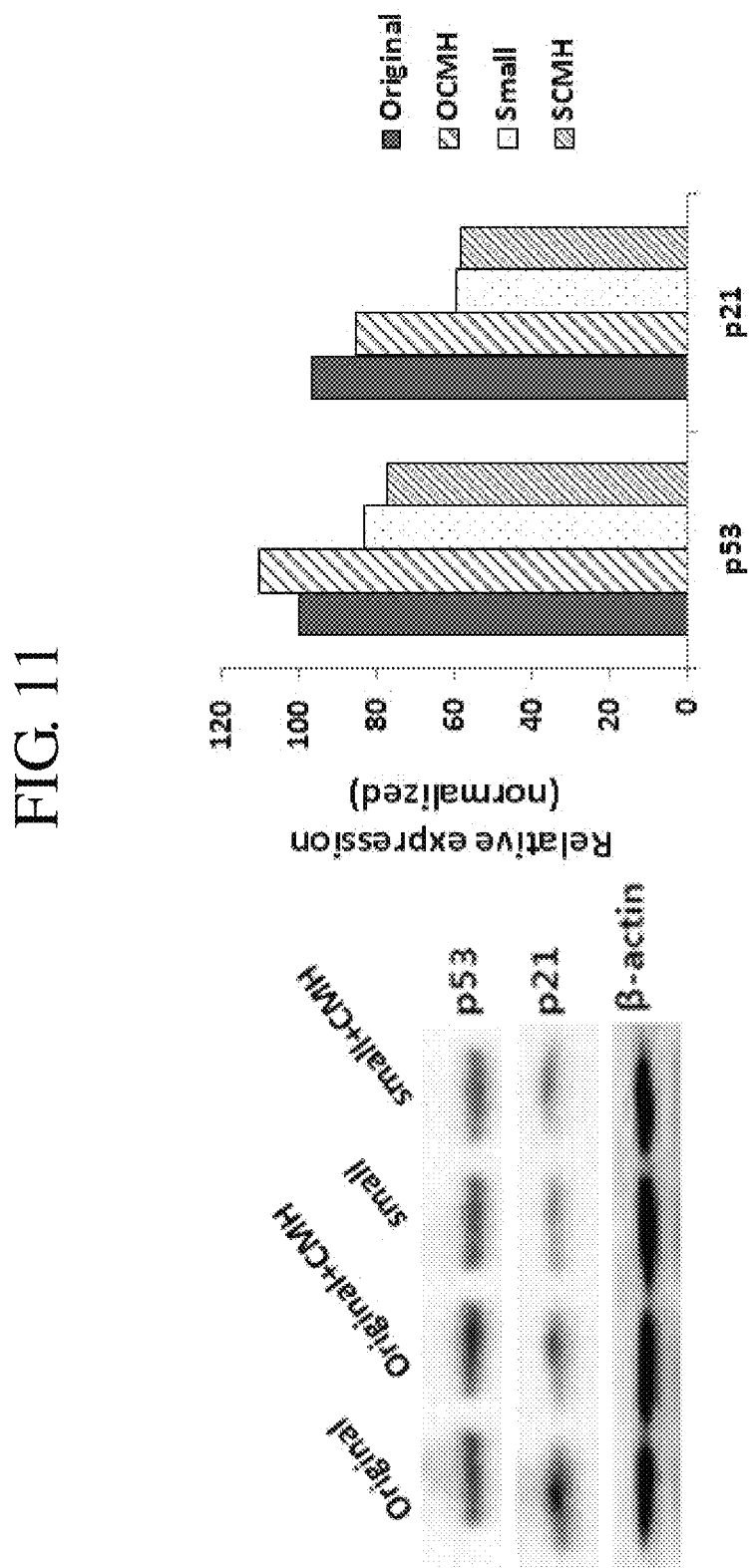

FIG. 11 provides results of Western blot and a quantitation graph showing the expression levels of p53 and p21 (proliferation inhibitory markers) after culturing the original cell group and small cell group under a conventional culture condition and a CMH condition.

Figure 12A:
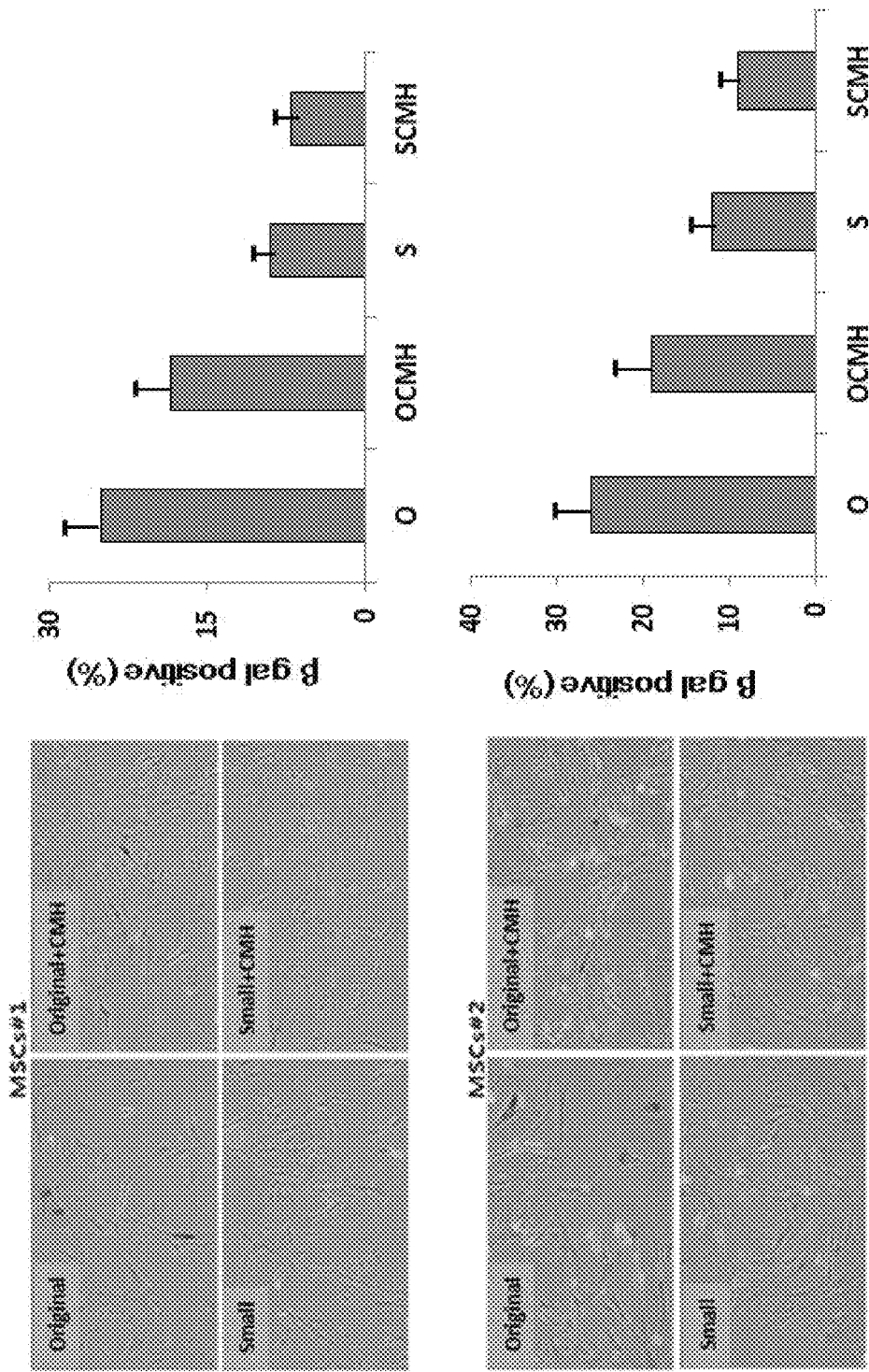
Figure 12B:
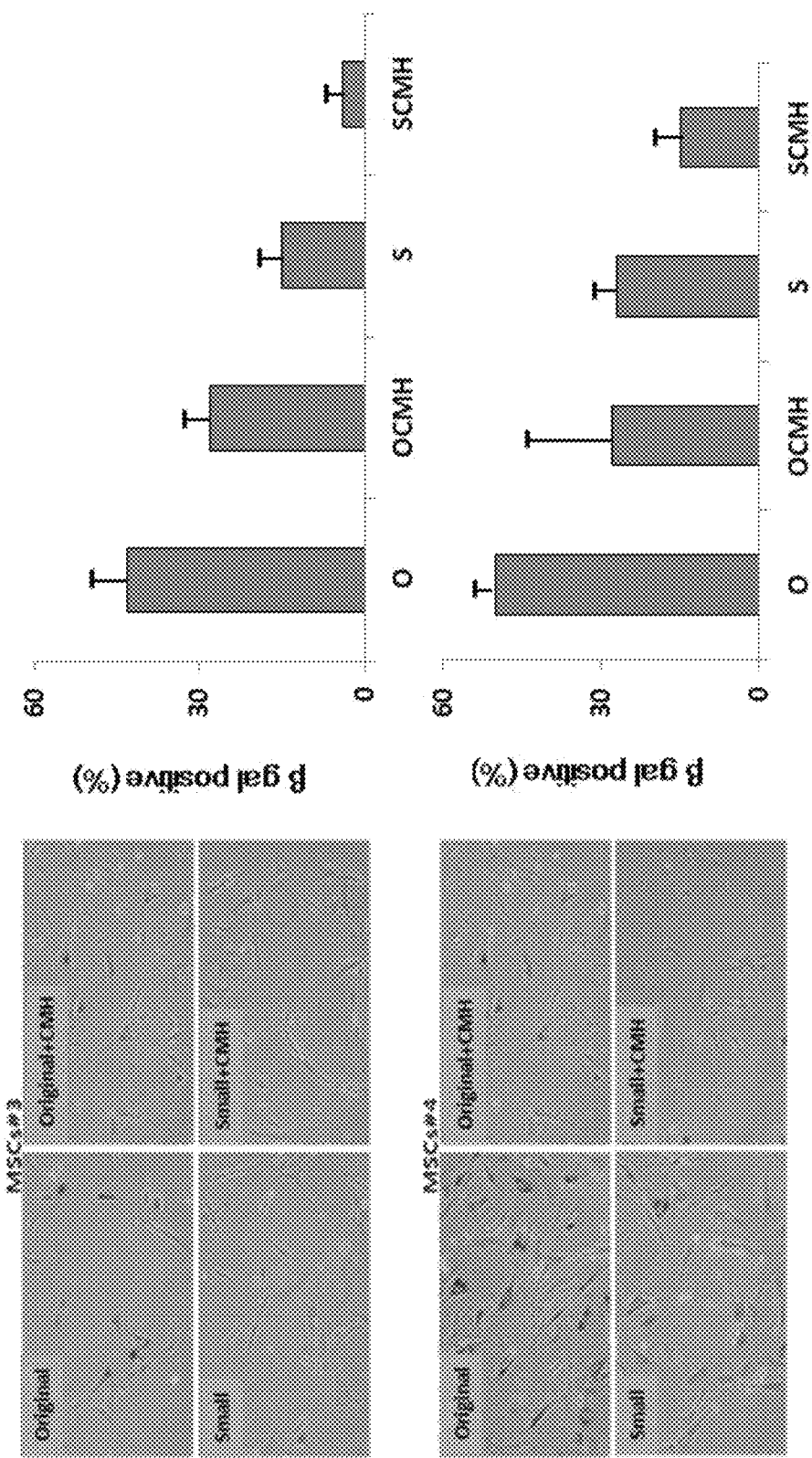

FIGS. 12A and 12B provide photographs of aged cells which were stained, and graphs showing the ratio of the stained cell counts to the total cell counts, after culturing the original cell group and the small cell group with several passages under a conventional culture condition and a CMH culture condition, and inducing senescence of the cells.

Figure 13:
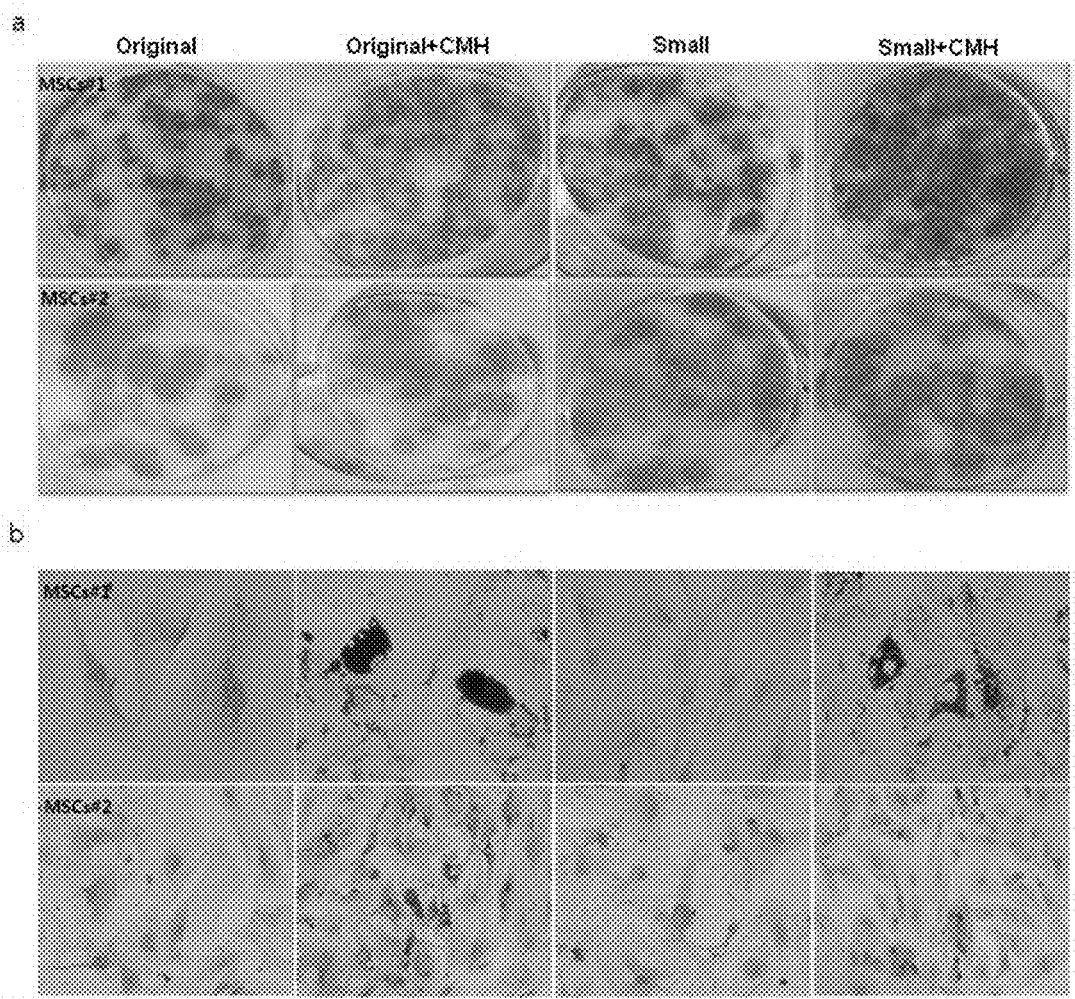

FIG. 13 provides photographs showing osteogenic induction (a) and adipogenic induction (b) after culturing the original cell group and the small cell group under a conventional culture condition and a CMH culture condition.

DETAILED DESCRIPTION OF THE INVENTION

The present invention provides a method for culturing mesenchymal stem cells, comprising the steps of (1) isolating mesenchymal stem cells having a size of 8 μm or less; and (2) culturing the isolated mesenchymal stem cells in a medium containing 2.1 to 3.8 mM of calcium and 1.0 to 3.0 mM of magnesium under a condition of 2 to 5% oxygen.

The present invention is based on the discovery that mesenchymal stem cells having a size of 8 μm or less have greater proliferative capacity than those of other size, and the proliferative capacity and differentiation potential of the mesenchymal stem cells can be further improved by culturing them in a medium containing specific concentrations of calcium and magnesium under a hypoxic condition.

In a method for culturing mesenchymal stem cells of the present invention, step (1) is a step of isolating the mesenchymal stem cells having a size of 8 μm or less.

The culturing method of the present invention may be applied to mesenchymal stem cells of various origins. Examples of the mesenchymal stem cells useful in the present invention include those derived from umbilical cord blood, bone marrow, lipid, muscle, skin, amniotic fluid, umbilical cord, or teeth, but are not limited thereto. In one preferred embodiment of the present invention, the culturing method of the present invention is applied to umbilical cord blood-derived mesenchymal stem cells.

In addition, the mesenchymal stem cells to which the culturing method of the present invention can be applied may be derived from various subjects. For example, the mesenchymal stem cells useful in the present invention may be obtained from mammals including humans, but are not limited thereto. In one preferred embodiment of the present invention, mesenchymal stem cells of human origin are used.

While conventional mesenchymal stem cells have a size range of 3.5 to 24 μm, the mesenchymal stem cells used in the present invention are characterized by having a size of 8 μm or less (small). Mesenchymal stem cells having a size of 8 μm or less have superior proliferative capacity to that of non-isolated mesenchymal stem cells (hereinafter referred to as "original cells") or mesenchymal stem cells with a size exceeding 8 μm.

In a method of the present invention, the isolation of mesenchymal stem cells having a size of 8 μm or less can be carried out preferably using a filter, although there is no particular restriction. The filter may be selected considering the risk of damaging mesenchymal stem cells and safety in usage such as, for example, Xiaogan yaguang's filtration membrane tube. The method for isolation using the filter may be conducted under the optimum condition for obtaining small cells. For example, mesenchymal stem cells at the population of $2\times10^5$ cells may be loaded on a filtration membrane tube having a pore size of 8 μm, and centrifuged once at 1,200 rpm for 5 minutes, to obtain homogeneous mesenchymal stem cells having a size of 8 μm or less.

The mesenchymal stem cells having a size of 8 μm or less is hereinafter referred to as "small cells".

Step (2) of a method for culturing mesenchymal stem cells of the present invention is a step of culturing the mesenchymal stem cells having a size of 8 μm or less in a medium containing 2.1 to 3.8 mM of calcium and 1.0 to 3.0 mM of magnesium under a hypoxic condition of 2 to 5% oxygen.

The culturing method is primarily characterized by culturing the mesenchymal stem cells in a medium containing calcium and magnesium.

The culture medium may be prepared from a conventional culture medium for stem cells by adjusting the concentrations of calcium and magnesium. Examples of the conventional culture media include Dulbecco's modified eagle medium (DMEM), minimal essential medium (MEM), α-MEM, McCoys 5A medium, eagle's basal medium, Connaught Medical Research Laboratory (CMRL) medium, Glasgow minimal essential medium, Ham's F-12 medium, Iscove's modified Dulbecco's medium (IMDM), Leibovitz's L-15 medium, Roswell Park Memorial Institute (RPMI) 1640 medium, medium 199, and Hank's medium 199, but are not limited thereto.

Optionally, the culture medium may or may not contain a serum. In addition, a serum replacement may be used, instead of a serum, in the culture medium.

In one embodiment of the present invention, the culture medium contains 5 to 30% of fetal bovine serum (FBS). In another embodiment, the culture medium contains a serum replacement. In addition to a commercially available product, various growth factors in a human serum or a human platelet lysate, including PDGF, TGF, IGF, and cytokines similar thereto may be used as a serum replacement.

In the culturing method of the present invention, calcium functions to promote the proliferation of mesenchymal stem cells, with the suppression of immunogenicity and the stimulation of cytokine secretion. In this regard, calcium may be used at the concentration of 2.1 to 3.8 mM in the medium, preferably at the concentration of 3.3 to 3.8 mM, and more preferably at the concentration of about 3.6 mM. For instance, when α-MEM is adopted as the culture medium, calcium may be added at the concentration of 0.3 to 2.0 mM, preferably at the concentration of from 1.5 to 2.0 mM, and more preferably at the concentration of about 1.8 mM because the medium already contains 1.8 mM of calcium. Likewise, when another medium is adopted, the calcium concentration to be added to achieve the desired concentration necessary for the culturing method of the present invention can be readily calculated in consideration of the calcium concentration of the medium itself.

In a culture medium of the present invention, magnesium is employed to prevent the precipitation of calcium. Magnesium may be used at the concentration of 1.0 to 3.0 mM in the medium, and preferably at the concentration of approximately 1.8 mM. When magnesium is present at the concentration of less than 1.0 mM in the culture medium, it is difficult to prevent the precipitation of calcium. On the other hand, a magnesium concentration higher than 3.0 mM in the culture medium is likely to block the formation of the extracellular matrix (ECM), interfere with the adherence of the cells to the bottom of the culture dish, thus rendering them susceptible to shear stress, and increase intracellular mineralization. For instance, when α-MEM is adopted as a culture medium, magnesium may be added at the concentration of 0.2 to 2.2 mM, and preferably at the concentration of 1.0 mM because the medium already contains 0.8 mM of magnesium. Likewise, when another medium is adopted, the magnesium concentration to be added to achieve the desired concentration necessary for the culturing method of the present invention can be readily calculated in consideration of the magnesium concentration of the medium itself.

Thus, a culture medium according to a preferred embodiment of the present invention may be based on α-MEM supplemented with 5 to 30% of fetal bovine serum (FBS), 0.3 to 2.0 mM of calcium, and 0.2 to 2.2 mM of magnesium, thereby making final concentrations of calcium and magnesium to 2.1 to 3.8 mM and 1.0 to 3.0 mM, respectively.

Furthermore, another feature of the culturing method of the present invention is a hypoxic culturing condition for mesenchymal stem cells. Compared to a normal oxygen condition (normoxia), the hypoxic condition promotes the proliferation of mesenchymal stem cells, with the suppression of immunogenicity and the stimulation of cytokine secretion. In this context, the hypoxic condition indicates an oxygen content of 2 to 5%. A problem associated with an oxygen concentration below 2% or over 5% is a significant decrease in the proliferation of mesenchymal stem cells. In one preferred embodiment of the present invention, mesenchymal stem cells are cultured in about 3% level of oxygen. A hypoxic condition may be achieved by adjusting the oxygen concentration in a cell incubator. For example, an incubator may be supplied with nitrogen gas (100%) or nitrogen/carbon dioxide mixture gas (95%/5%) to change a normoxic atmosphere to a hypoxic atmosphere. The oxygen concentration in an incubator may be monitored by an oxygen sensor equipped on the incubator.

Except for the aforementioned conditions of the present invention, mesenchymal stem cells may be cultured in a conventional manner. For example, mesenchymal stem cells may be cultured in a three-dimensional bioreactor or spinner or a conventional adherent culture vessel.

When a first feature for the concentration control of calcium and magnesium is combined with a second feature for a hypoxic condition, a synergistic effect can be obtained. That is, a combination of the particular concentration of calcium and magnesium and a hypoxic condition allows mesenchymal stem cells to proliferate more efficiently, with a higher improvement in the suppression of immunogenicity and the stimulation of cytokine secretion, compared to the individual conditions. The combined condition for a culturing method of the present invention is referred to as "CMH condition" (calcium+magnesium+hypoxic condition).

A culturing method of the present invention may be applied to passages of mesenchymal stem cells. In other words, the mesenchymal stem cells cultured using a culturing method of the present invention can be sub-cultured in the same manner. By allowing mesenchymal stem cells to proliferate more efficiently, a culturing method of the present invention has the advantage of producing a greater number of mesenchymal stem cells even when fewer passages are performed. For instance, after 5 passages in which the same number of cells were inoculated and cultured for a uniform duration at each passage, a culturing method of the present invention is found to produce mesenchymal stem cells 100 to 1,000-fold greater in number than that of conventional methods.

Accordingly, the present invention provides mesenchymal stem cells prepared by the above method, which are improved in proliferative capacity and differentiation potential.

In addition, the present invention provides a cell therapeutic agent including mesenchymal stem cells obtained by the above culture method. A cell therapeutic agent of the present invention can be applied in the regeneration or protection of adipocytes, osteocytes, chondrocytes, myocytes, neurocytes, cardiomyocytes, hepatocytes, islet beta cells, vascular cells, or pneumocytes. In addition, a cell therapeutic agent of the present invention is useful for one selected from the group consisting of the treatment of pulmonary diseases; the suppression or treatment of lung disease-induced inflammation; the regeneration of pulmonary tissues; and the suppression of pulmonary fibrosis.

Particularly, it can be used to suppress or improve pulmonary disease-induced inflammation and fibrosis. Further, a cell therapeutic agent of the present invention can be applied to the therapy of cardiovascular diseases or the regeneration of cartilage. Moreover, a cell therapeutic agent of the present invention can improve immunomodulative functions; reduce one of immune responses, immune cell penetration, or immunogenicity; and suppress inflammatory reactions.

Hereinafter, the present invention will be described in detail with examples, but the examples do not confine the scope of the present invention.

Example 1: Analysis of Cell Size of Cord Blood-Derived Mesenchymal Stem Cells

The cell size of non-isolated cord blood-derived mesenchymal stem cells was measured as follows.

Specifically, cord blood-derived mesenchymal stem cells were obtained from 4 donors and were kept frozen. Each collection of the mesenchymal stem cells was thawed and cultured in an incubator having α-MEM medium supplemented with 10% FBS, under the condition of 37° C. and 5% $CO_2$ for 5 days.

The morphology of the cells was observed with a microscope, and single cells were obtained by treatment with trypsin. The single cells were treated with trypan blue to examine survival rate. The cells were observed with ECLIPSE TE2000-U inverse microscope (Nikon) at 100× magnification, and multiple regions of the cell population were photographed. At the photographed regions, the size of live cells was analyzed using Cellometer vision 5× (nexcelom biosceince).

Figure 1:
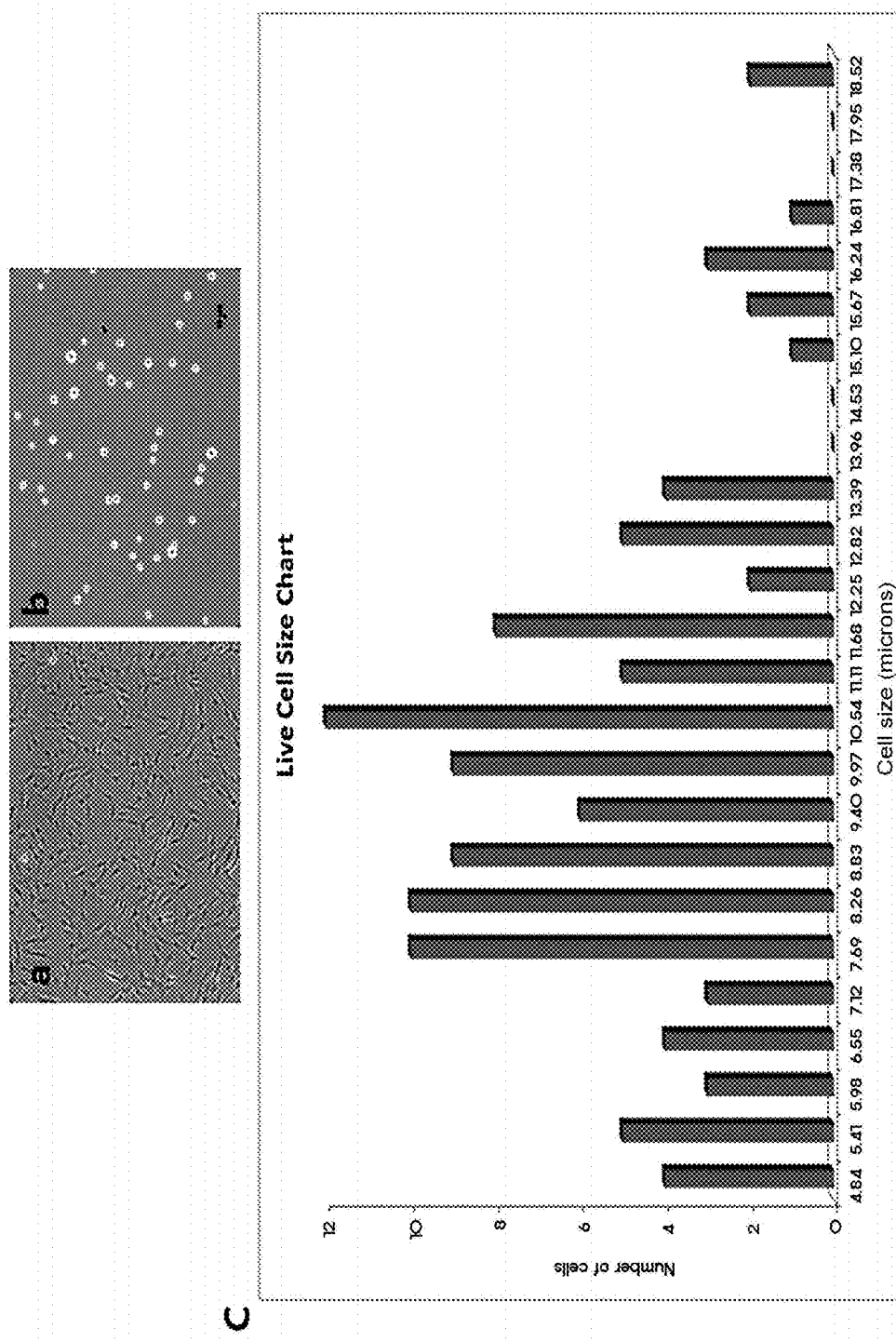
FIG. 1 shows photographs of mesenchymal stem cells, in the form of being attached before trypsin treatment (FIG. 1a)

FIG. 1 shows the photographs taken with the microscope. FIG. 1a is a photograph showing cultured mesenchymal stem cells isolated from cord blood, and FIG. 1b is a photograph showing mesenchymal stem cells in the form of single cells after trypsinization. FIG. 1c is a graph showing results of measurement of the cell size.

As can be seen from FIG. 1, no information on cell size could be obtained when the cells were adherent to each other (FIG. 1a), but cell size could be examined when the cells were in the form of single cells (FIG. 1b). Upon analysis with Cellometer, it was confirmed that mesenchymal stem cells constitute a heterogeneous population of cells with various sizes ranging from 4.84 to 18.52 μm (FIG. 1c).

Example 2: Analysis on Proliferative Capacity of Cord Blood-Derived Mesenchymal Stem Cells According to their Size In order to analyze the correlation between the cell size and the proliferative capacity of cord blood-derived mesenchymal stem cells, the mesenchymal stem cells obtained from four donors (MSCs #1 to #4) were cultured by the method described in Example 1, and then, cell size was analyzed using Cellometer. Results of the analysis are shown in FIGS. 2A and 2B. It was confirmed that cell size of MSCs #1 and #2 was relatively small as can be seen from FIG. 2A, whereas cell size of MSCs #3 and #4 was relatively large as can be seen from FIG. 2B.

Group I (MSCs #1 and #2) having a small cell size and Group II (MSCs #3 and #4) having a large cell size were cultured with passages, and cumulative growth curves were prepared. The cumulative growth curve is expressed as cumulative population doubling (CPD) which is a cumulative value of population doubling (PD).

The PD is calculated based on a total number of cells of each passage, which is log (proliferation rate of a specific passage)/log 2. When cells of a specific passage reach 50 to 60% of confluence, they are trypsinized and separated, to harvest single cells. The proliferation rate of a specific passage was calculated by dividing the number of the harvested single cells by the number of cells which had been initially provided to the culture vessel. These procedures were repeated until a passage at which proliferation of cells stopped. Cells were allowed to proliferate starting from the first and second passages until the last passage at which proliferation of cells stopped. The period of culture per passage was 7 days. P1 to P10 in the graph refers to the number of passages. The experimental results are shown in FIG. 3.

As can be seen from FIG. 3, it was confirmed that the proliferative capacity in Group I having a small cell size was greater than Group II having a large cell size, and that the proliferation of cells in Group I lasted longer than Group II.

Example 3: Determination of Cell Size and Isolation of Small Cells

<3-1> Determination of Cell Size Suitable for Isolation

As a filter for analyzing cells according to their size, Xiaogan yaguang's filtration membrane tube was selected. The filter can be protected from contamination from outside during centrifugation, owing to its installation inside a 50 mL tube. Meanwhile, equipments for isolating cells are known, such as sorting equipment, Beckman's high speed centrifuge, BD's Transwell® and the like. But, the sorting equipment is not suitable for a procedure of manufacturing therapeutic agents due to possibility of damaging cells during a separation process of cells. Beckman's high-speed centrifuge equipment is not suitable for use in a GMP manufacturing process because it does not utilize disposable products for consumable parts. As for Transwell®, not being a sealed system, it does not guarantee aseptic condition of cells during centrifugation. Considering that the mesenchymal stem cells of the present invention should be used as a therapeutic agent, Xiaogan yaguang's filtration membrane tube suitable for the actual GMP manufacturing facility was determined to be best suited.

Using the filtration membrane tube, cord blood-derived mesenchymal stem cells having a size of 3 μm or less (≤3 μm), 5 μm or less (≤5 μm), and 8 μm or less (≤8 μm) were isolated. The amount of each of the isolated cells was measured. As a result, the amount of the cells having a size of ≤3 μm or ≤5 μm isolated by the filter, as well as the percentage of said cells among mesenchymal stem cell population, was too low. In contrast, the mesenchymal stem cells having a size of 8 μm or less were obtained in a sufficient amount. As such, a suitable cell size was determined to be 8 μm or less, and the cells of this size range are referred to as "small cells" or "small mesenchymal stem cells."

<3-2> Establishing the Optimal Conditions for the Acquisition of Small Cells

In order to establish the optimum conditions for the acquisition of cells having a size of 8 μm or less, centrifuging conditions (speed and time duration of centrifugation), the number of loaded cells and the cell acquisition rate according to the number of repetitions of centrifugation were investigated.

(1) Cell Acquisition Rate According to the Centrifuging Speed

Cultured mesenchymal stem cells ($2\times10^5$ cells/2 mL) in Example 1 were centrifuged using a centrifuge (Hanil Science Industrial, combi514R) at 800 rpm, 1,200 rpm, 1,500 rpm and 2,000 rpm respectively for 5 minutes. The ratio (%) of cells that passed through the filter after the centrifugation was measured setting the number of cells which had been loaded on the filter ($2\times10^5$ cells) as 100%. The results are shown in Table 1.

TABLE 1

|  | 800 rpm, 5 min | 1,200 rpm, 5 min | 1,500 rpm, 5 min | 2,000 rpm, 5 min |
|---|---|---|---|---|
| Acquisition rate (%) | 17.9 | 100.0 | 82.1 | 82.1 |
|  | 17.9 | 82.1 | 53.6 | 53. |
|  | 53.6 | 82.1 | 82.1 | 100.0 |
| Average | 29.8 | 88.1 | 72.6 | 78.6 |
| Error | 20.6 | 10.3 | 16.5 | 23.4 |

As shown in Table 1, it was found that centrifugation at the speed of 1,200 rpm resulted in higher acquisition rate than other speeds. Based on the above results, in the experiments below, centrifugation was conducted at the speed of 1,200 rpm.

(2) Cell Acquisition Rate According to Time Duration of Centrifugation

Cultured mesenchymal stem cells ($2\times10^5$ cells/2 mL) in Example 1 were centrifuged using a centrifuge (Hanil Science Industrial, combi514R) at 1,200 rpm for 2 minute, 5 minutes and 10 minutes, respectively, and then, the ratio of cells that passed through the filter were measured in the same manner as described above. The results are shown in Table 2.

TABLE 2

|  | 1,200 rpm, 2 min | 1,200 rpm, 5 min | 1,200 rpm, 10 min |
|---|---|---|---|
| Acquisition rate (%) | 53.6 | 100.0 | 100.0 |
|  | 35.7 | 71.4 | 82.1 |
|  | 100.0 | 71.4 | 53.6 |
| Average | 63.10 | 80.95 | 78.57 |
| Error | 33.18 | 16.50 | 23.42 |

As shown in the Table 2, it was found that centrifugation at 1,200 rpm for 5 minutes resulted in higher cell acquisition rate than other time durations. Based on the above results, in the experiments below, centrifugation was conducted at 1,200 rpm for 5 minutes.

(3) Cell Acquisition Rate According to the Number of Loaded Cells

Cultured mesenchymal stem cells in Example 1 were loaded on the filter at the population of $5\times10^4$, $1\times10^5$, $2\times10^5$ or $3\times10^5$ cells/2 mL, and centrifuged at 1,200 rpm for 5 minutes. Then, the ratio of cells that passed through the filter was measured in the same manner as described above. The results are shown in Table 3.

TABLE 3

|  | $5 \times 10^4$ cells | $1 \times 10^5$ cells | $2 \times 10^5$ cells | $3 \times 10^5$ cells |
|---|---|---|---|---|
| Acquisition rate (%) | 28.6 | 85.7 | 100.0 | 42.9 |
|  | 57.1 | 85.7 | 71.4 | 37.1 |
|  | 28.6 | 42.9 | 71.4 | 33.3 |
| Average | 38.10 | 71.43 | 80.95 | 37.76 |
| Error | 16.50 | 24.74 | 16.50 | 4.82 |

As shown in Table 3, it was found that loading mesenchymal stem cells at the population of $2\times10^5$ cells resulted in higher acquisition rate than other populations. In the experiments below, centrifugation was conducted by loading mesenchymal stem cells at the population of $2\times10^5$, and at 1,200 rpm for 5 minutes.

(4) Determining the Number of Centrifugation

In order to examine the cell acquisition rate according to the number of centrifugation, cells were divided into two groups, which were centrifuged once and twice, respectively. The group centrifuged twice was further divided into two sub-groups. In the second centrifugation of this latter, new culture medium was added to the centrifuging tube without replacing any filter in the first sub-group, whereas cells were suspended in the medium after replacing the filter in the second sub-group.

Specifically, in the first sub-group (twice (medium addition)), after centrifuging mesenchymal stem cells once as described above, 2 mL of new medium was added onto the used filter and the cells were centrifuged. Then, the number of cells that passed through the filter was measured in the same manner as described above. And in the second sub-group (twice (filter replacement)), after centrifuging mesenchymal stem cells once as described above, cells were harvested by suspending cells which were remaining on the filter. Then, a new filter was placed and the cells were centrifuged to measure the number of cells that passed through the filter. The results are shown in Table 4.

TABLE 4

|  | Once | Twice (medium addition) | | Twice (filter replacement) | |
|---|---|---|---|---|---|
|  | Once | Once | Twice | Once | Twice |
| Acquisition rate compared to the loaded cells (%) | 73.66 | 75.50 | 0.00 | 88.39 | 0.00 |
|  | 82.70 | 79.00 | 0.00 |  | 5.50 |
|  | 78.57 | 72.10 | 5.80 |  | 0.00 |
| Average | 78.31 | 75.53 | 5.80 |  | 5.50 |
| Total | 78.31 | 81.33 | | 87.15 | |
| Error | 4.53 | 3.45 | 3.35 | 5.84 | 6.06 |

As shown in Table 4, the two sub-groups centrifuged twice showed no significant difference from the group centrifuged once. As such, the number of centrifugation was finally determined to be one.

Upon observing the mesenchymal stem cells obtained under the optimum conditions with a microscope, it was confirmed that a uniform cell group having a cell size of 8 μm or less was obtained as shown in FIG. 4.

Example 4: Comparison on Proliferative Capacity of Mesenchymal Stem Cells (Small Cells) Having a Size of 8 μm or Less To examine proliferative capacity of small cells obtained according to the present invention, the mesenchymal stem cells were divided to a non-isolated cell group (original), a cell group with a cell size of 8 μm or less (small), and a cell group with a cell size exceeding 8 μm (large), and were cultured with passages to compare proliferative capacity. The aforementioned three types of cell groups were cultured in α-MEM culture medium supplemented with 10% FBS, with each passage being 5 days long on average to measure cumulative growth.

Figure 5:
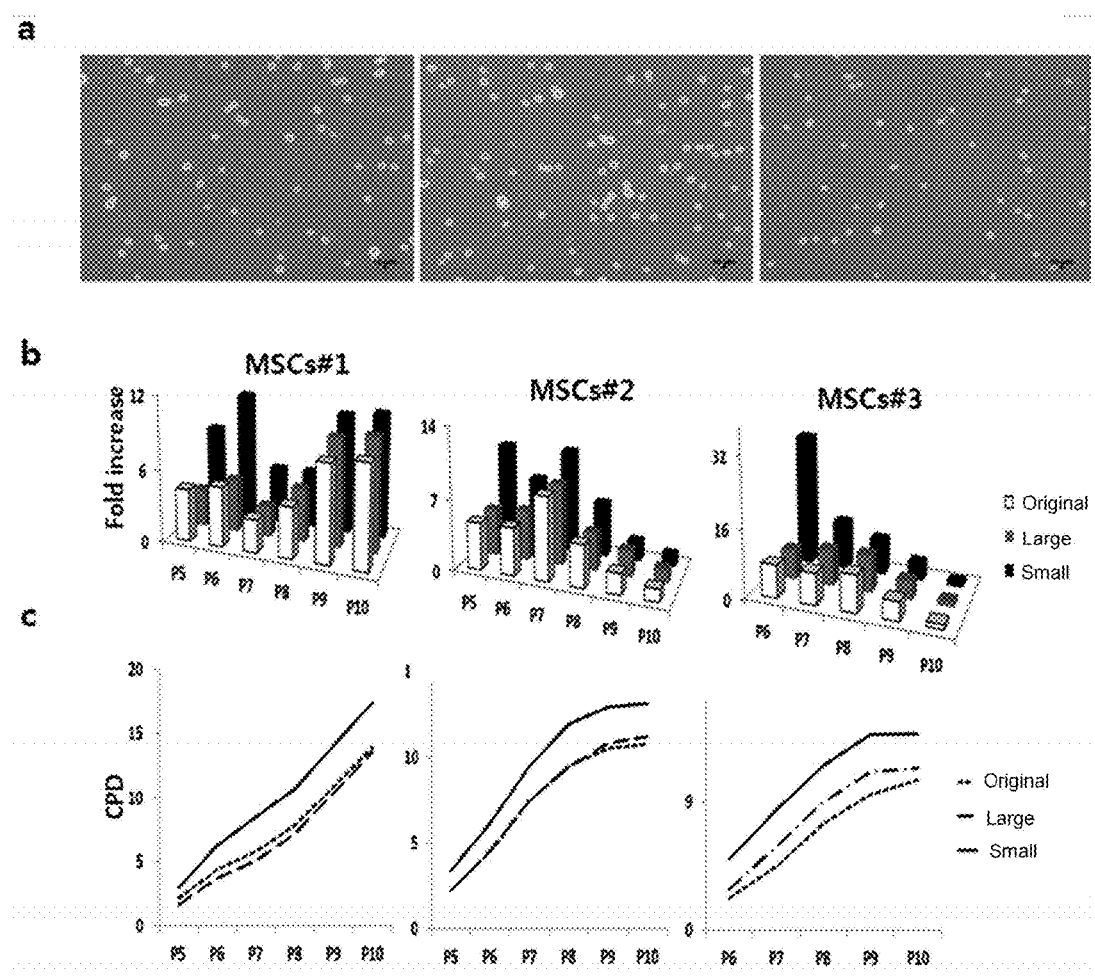

The results of the measurement are shown in FIG. 5. FIG. 5a shows microscopic photographs of three types of cell groups, indicating that the group having a cell size of 8 μm or less (right photo) was more homogeneous compared to original cell group (left photo) and a group having a cell size exceeding 8 μm (middle photo). FIGS. 5b and 5c show proliferative capacity and CPD, wherein proliferative capacity in the group having a cell size of 8 μm or less was much greater than other cell groups. In particular, the CPD in the group having a cell size of 8 μm or less was at least 2-fold greater than other 2 groups.

Example 5: Analysis on Proliferative Capacity According to the Percentage of Mesenchymal Stem Cells Having a Size of 8 mM or Less (Small Cell)

To demonstrate the superiority of proliferative capacity of mesenchymal stem cells having a size of 8 μm or less (small cells), 5 kinds of cell groups with different percentages of small cells were prepared as follows.

Group 1: MSCs exceeding 8 μm (100%)
Group 2: MSCs exceeding 8 μm (75%)+MSCs of 8 μm or less (25%)
Group 3: MSCs exceeding 8 μm (50%)+MSCs of 8 μm or less (50%)
Group 4: MSCs exceeding 8 μm (25%)+MSCs of 8 μm or less (75%)
Group 5: MSCs of 8 μm or less (100%)

The proliferative capacity of each cell group was measured by the same method as Example 2, and the amount of proliferative capacity is presented in FIG. 6 as a fold increase compared to Group 1.

As shown in FIG. 6, higher proliferative capacity of cells was observed as the percentage of cells having a size of 8 μm or less increased. These results show that cells having a size of 8 μm or less have a very high proliferative capacity.

Example 6: Analysis on Proliferation Capacity of Small Cells According to CMH Conditions The proliferative capacity of cord blood-derived mesenchymal stem cells is known to decrease due to increase of cell size when cultured with passages under conventional culture conditions (i.e., 37° C. and 5% $CO_2$). Therefore, it is necessary to establish culture conditions under which cord blood-derived mesenchymal stem cells of 8 μm or less having superior proliferative capacity can maintain their cell size and proliferative capacity.

Thus, in this example, cord blood-derived mesenchymal stem cells having a size of 8 μm or less were cultured under a variety of conditions, and then the cell size and proliferative capacity under those conditions were compared.

Specifically, the cells of an original cell group and a cell group having a cell size of 8 μm or less (small cell group) were thawed and cultured in an incubator (hypoxia/$CO_2$ incubator, Thermo Scientific #3131) containing α-MEM culture medium (Invitrogen, USA) supplemented with 10% FBS, under the condition of 37° C. and 5% $CO_2$ for 5 days. When the cells reached 80 to 90% confluence, single cells were obtained by treatment with trypsin. Then, the cells were inoculated to the α-MEM media at the concentration of 5000 cells/cm², and were cultured under a typical culture condition (the control group), additional calcium (including magnesium) condition, hypoxic condition, and additional calcium (including magnesium)/hypoxic condition (hereinafter referred to as "CMH"). In case of a typical culture condition, cells were cultured in α-MEM medium (containing 10% FBS; containing 1.8 mM of calcium and 0.8 mM magnesium) under the condition of 37° C., 5% $CO_2$, and normoxia (atmospheric oxygen concentration of 21% (v/v)). And in case of additional calcium (including magnesium) condition, cells were cultured in α-MEM medium whose total concentrations of calcium and magnesium were adjusted to 3.6 mM and 1.8 mM by adding 1.8 mM of calcium and 1 mM of magnesium, respectively, under the condition of 37° C., 5% $CO_2$, and the normoxia. Further, in case of the hypoxic conditions, cells were cultured in α-MEM medium under the condition of 37° C., 5% $CO_2$, and hypoxia (oxygen concentration of 3% (v/v)). In case of a CMH condition, cells were cultured in α-MEM medium whose total concentrations of calcium and magnesium were adjusted to 3.6 mM and 1.8 mM by adding 1.8 mM of calcium and 1 mM of magnesium, respectively, under the condition of 37° C., 5% $CO_2$, and 3% (v/v) oxygen. The shape and proliferative capacity of the cells of each group were observed during 4 rounds of culture passages.

The shape (a, b) and proliferative capacity (c) of the cells are shown in FIG. 7. As shown in FIGS. 7a and 7b, the cell density of the original cell group and the small cell group cultured under the CMH condition was shown to be significantly higher than that of groups cultured under other conditions. Further, when the shape of the cells of the original cell group and the small cell group were compared, the small cell group had identical forms of cell attachments and had larger amount of attached cells.

On the other hand, as can be seen from FIG. 7c, in both of the control cell group and the small cell group, proliferative capacity was shown to be greatest under the CMH condition. In particular, proliferative capacity per passage of the small cell group was at least 2-folds greater than that of none-cell group. And the results on the proliferative capacity of the small cell group per passage showed that the cells cultured under the CMH condition had at least 2-fold greater proliferative capacity than those cultured under the normal condition.

The above results indicate that the small cell group has a greater proliferative capacity than the original cell group, and that cell size can be maintained and proliferative capacity of the cells can be enhanced by culturing the small cells under the CMH condition.

Example 7: Analysis on Cell Size and Proliferative Capacity of Small Cell Group Cultured Under CMH Condition To analyze the size and proliferative capacity of cord blood-derived mesenchymal stem cells of the small cell group cultured under the CMH condition, the original cell group and the small cell group having a cell size of 8 μm or less were cultured under the typical culture condition and the CMH condition. Such mesenchymal stem cells were cultured with 2 rounds of passages (p2) under a typical culture condition before culturing them with passages under each condition. These cells were cultured for 7 days after each passage. Then, proliferative capacity and cumulative proliferative capacity of the cells were measured. The results are shown in FIG. 8.

Figure 8A:
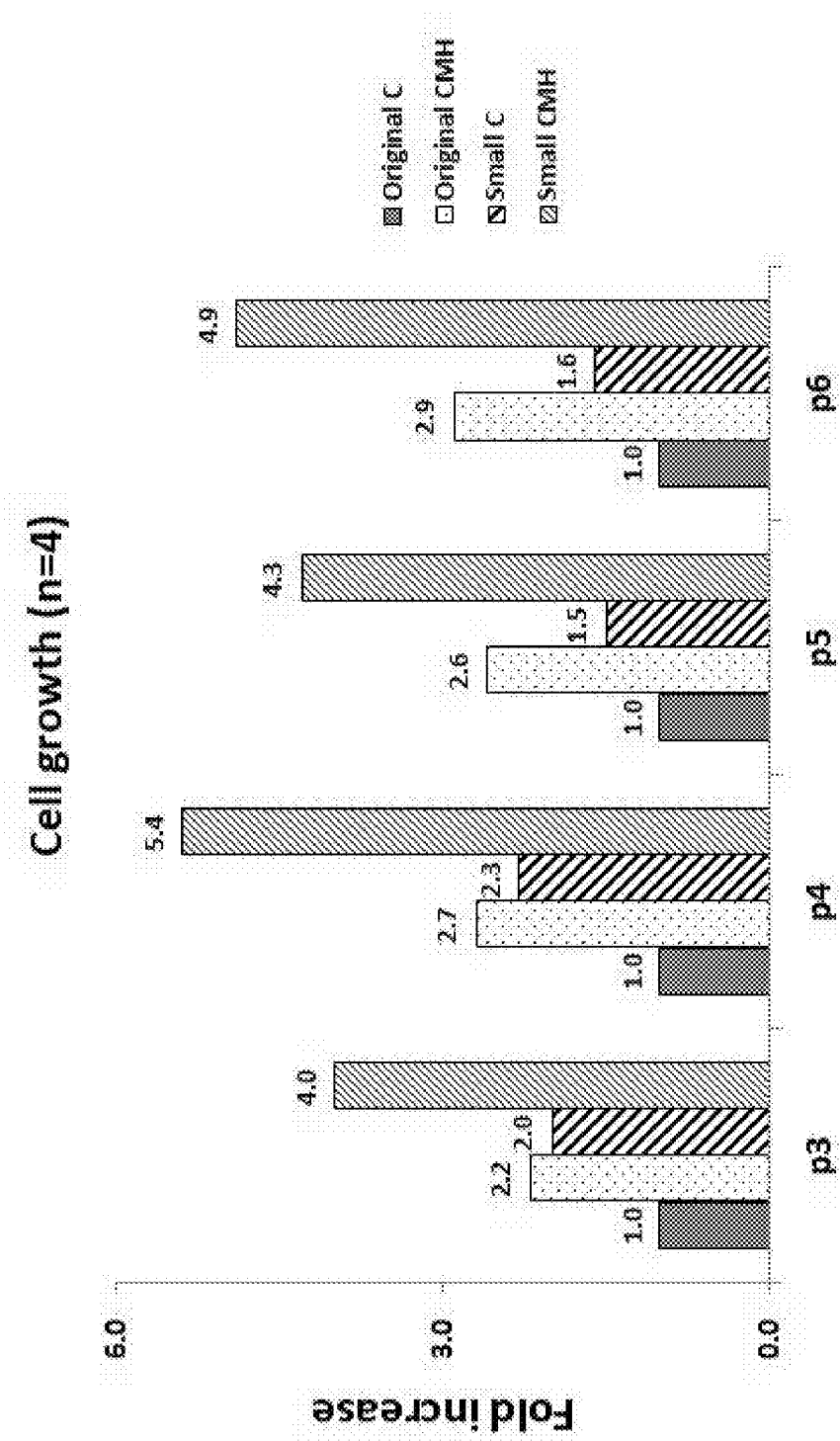
Figure 8B:
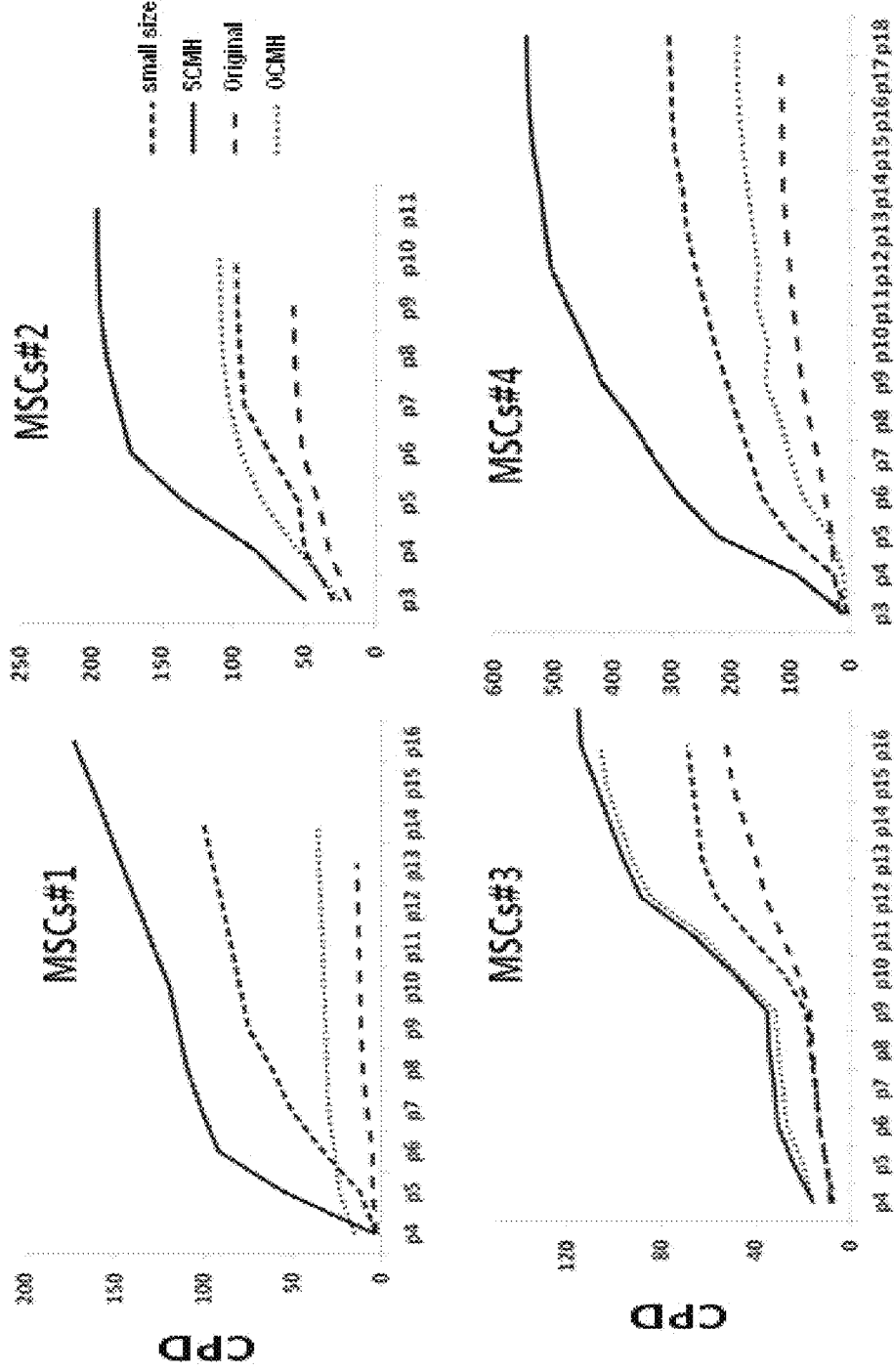

As shown in FIG. 8, the maintenance of cell size and proliferative capacity was greatly enhanced when the small cell group was cultured under the CMH condition, which effect was maintained during continuing passages. The proliferative capacity was observed to be remarkably high during initial passages (p3 to p6) which are used in actual cell therapy. In particular, the combination of the small cell group and the CMH condition showed at least 2-fold difference in proliferative capacity per passage (FIG. 8A). In case of cumulative population doubling (CPD), it was found that the proliferative capacity of the cells was maintained throughout multiple passages (FIG. 8B), although there were some variations among the MSCs.

These results indicate that a combination of the small cell group and the CMH culture condition of the present invention is effective in improving proliferation of cord blood-derived mesenchymal stem cells.

Example 8: Proliferative Capacity of Mesenchymal Stem Cells According to Calcium Concentration To examine the proliferative capacity of umbilical cord blood-derived mesenchymal stem cells according to calcium concentration, the cells were cultured in media with various concentrations of calcium.

Specifically, umbilical cord blood-derived mesenchymal stem cells (MSC #1) which had been collected from a mother after delivery and stored in a frozen state were thawed, and cultured in an incubator (hypoxia/$CO_2$ incubator, ThermoScientific #3131) which contains α-MEM medium (Invitrogen, USA) supplemented with 10% FBS, at 37° C. under 5% $CO_2$ condition. When the cells reached 50 to 96% confluence, they were separated into single cells by treatment with trypsin. To the α-MEM (supplemented with 10% FBS; containing 1.8 mM calcium and 0.8 mM magnesium), various concentrations (0 mM, 1.6 mM, 1.8 mM, 2.0 mM, 2.2 mM, 2.4 mM and 2.6 mM) of calcium were added so that the final calcium concentrations of the media were adjusted as follows: 1.8 mM, 3.4 mM, 3.6 mM, 3.8 mM, 4.0 mM, 4.2 mM and 4.4 mM. The cells were cultured in the media for 6 days, and then were counted. In order to prevent calcium-induced precipitation, magnesium was added at the concentration of 1 mM to each medium (total magnesium concentration was 1.8 mM). The cells were cultured under 21% (v/v) normoxic condition. When cells grew to the extent of 50 to 60%, they were cultured with passages in the same way. The examination results are shown in FIG. 9.

As can be seen from FIG. 9, the proliferative capacity increased over an additional calcium concentration range from 0 to 1.8 mM (total calcium concentration of 1.8 or 3.6 mM in the medium). From these results, the optimal calcium concentration for achieving the maximal proliferation of cells was 3.6 mM in a medium. Thus, it is considered advantageous to culture cells in a medium with a calcium concentration of 1.8 to 3.6 mM in order to achieve greater proliferative capacity compared to a typical culture condition.

Example 9: Proliferative Capacity of Umbilical Cord Blood-Derived Mesenchymal Stem Cells According to Oxygen Concentration To examine the proliferative capacity of umbilical cord blood-derived mesenchymal stem cells according to oxygen concentration, the cells were cultured under conditions with various concentrations of oxygen.

Specifically, umbilical cord blood-derived mesenchymal stem cells (MSC #1) were cultured in the same manner as in Example 8 in α-MEM supplemented with 10% FBS, but calcium and magnesium were not additionally added, and cells were cultured under 3% or 5% oxygen, or under a normoxic condition (oxygen level in air, 21%), and were counted. The results are shown in FIG. 10.

As shown in the results, proliferation capacity of cells was greater under a hypoxic condition than a normoxic condition. Especially, proliferation capacity was greatest under the oxygen concentration of 3%, which result was maintained throughout continuing passages for a long period.

Example 10: Analysis on Proliferation-Inhibitory Protein and Senescence of Umbilical Cord Blood-Derived Mesenchymal Stem Cells According to Culture Conditions To identify the cause of the improvement in the proliferation of the umbilical cord blood-derived mesenchymal stem cells in Example 6, the expression level of proliferation-inhibitory protein in stem cells and changes in senescence thereof were examined.

Specifically, as described in Example 6, the original cell group and the small cell group were cultured under the typical culture condition and the CMH condition. When cells reached 50 to 60% confluence, they were detached by treatment with trypsin. Subsequently, cell culture solution was centrifuged to remove the medium, and then was washed with PBS to obtain cells. Next, protein was isolated from the cells using a lysis buffer (RIPA) according to the manufacturer's protocol. The protein was quantified using bovine serum albumin (BSA) as a standard, and 15 μg of the protein was prepared to perform Western blot. The protein was loaded onto 12% polyacrylamide gel, and then was electrophoresed at 130 V for 2 hours. After the electrophoresis, the protein was transferred from the gel to a nitrocellulose membrane (Amersham Pharmacia, USA) with a current of 300 mA for 3 hours using Western Blotter, and the membrane was blocked for 1 hour using 1×TBST (100 mM Tris (pH 7.5), 1.5 M NaCl, 0.5% Tween-20) solution containing 5% fat-free milk. Then, primary antibodies (p21, p53 (Abcam, USA) and β-actin) were attached to the blocked nitrocellulose membrane, at a refrigeration temperature overnight. Thereafter, the resultant nitrocellulose membrane was washed with 1× TBST, and secondary antibodies (anti-rabbit or mouse IgG-HRP, Cell Signaling Technology, MA, USA) were added and allowed to attach thereto for 1 hour at room temperature. Next, ECL prime solution was poured on the membrane by using ECL Western blotting detection kit (Amersham Pharmacia) according to the manufacturer's protocol and bands were examined by Chemidoc equipment (Biorad, USA).

Results of the Western blot are shown in FIG. 11. As shown in FIG. 11, it was found that the expression levels of p53 and p21 (Abcam), proliferation-inhibitory proteins, were relatively low in the small cell group which had been cultured under the CMH condition. This result indicates that the CMH culture condition improves proliferative capacity of the mesenchymal stem cells by down-regulating the expression of the proliferation-inhibitory proteins.

Meanwhile, cells of the original cell group and the small cell group were cultured with several passages under the typical culture condition and the CMH condition to induce senescence of them. Culture solution was removed from each culture vessel and cells were washed once with PBS. Then, after adding 1 mL of 1× fixation solution (Cell Signaling Technology) thereto, the cells were cultured for 10 minutes at room temperature. After removing the fixation solution, the cells were washed twice with 2 mL of PBS. Next, after adding 1 mL of a β-galactosidase staining solution (SA β gal, Cell Signaling Technology) thereto, the cells were cultured in the incubator for 24 to 48 hours. And then, after removing the staining solution, the cells were washed with 1 mL of PBS. Then, the stained cells were photographed using ECLIPSE TE2000-U inverse microscope (Nikon) at 100× magnification. The photographs were utilized to examine the stained cell count relative to the total cell count.

Results of the examination are given shown in FIG. 12A and FIG. 12B. FIG. 12A and FIG. 12B (left) provide photographs of the original cell group and the small cell group of MSCs (MSCs #1 to #4) obtained from different mothers who had given birth, which were cultured in the typical culture condition and CMH condition. The photographs show the stained aged cells. Also, FIGS. 12A and 12B (right) provide graphs showing the ratio of the stained cell count to the total cell count. In the graphs, Original (O) refers to an original cell group, OCMH to an original cell group cultured under the CMH condition, S to a small cell group cultured under the conventional culture condition, and SCMH to a small cell group cultured under the CMH condition.

As shown in FIG. 12A and FIG. 12B, the number of aged cells was least when small cells were cultured under the CMH condition, as confirmed in the graphs. These results indicate that the proliferative capacity can be increased and senescence can be suppressed by culturing small cells of the present invention in the CMH condition.

Example 11: Examination of Changes in Differentiation Potential and Markers of Umbilical Cord Blood-Derived Mesenchymal Stem Cells According to the Culture Conditions In order to examine umbilical cord blood-derived mesenchymal stem cells for any changes in their basic features when small cells according to the present invention are cultured under the CMH condition, the original cell group and the small cell group from two kinds of umbilical cord blood-derived mesenchymal stem cells were cultured under the conventional culture condition and the CMH culture condition. Analysis was made to check any changes in differentiation potentials of mesenchymal stem cells in osteogenic and adipogenic inductions, and changes in labeling markers thereof.

<11-1> Osteogenic Induction and Bone Staining

For the induction of osteogenic differentiation, 500-1000 cells were placed in each well of a 6-well plate, and an osteogenic induction medium (10 mM glycerol phosphate, 50 mM L-ascorbic acid-2-phosphate, 1 μM dexamethasone/UVAB, α-MEM medium supplemented with gentamycin and 10% FBS) was provided after 2-4 days. The medium was replaced with new differentiation medium every 3 days to induce differentiation of the cells for 2-3 weeks. The differentiated cells were washed twice with PBS and then incubated in a fixation solution (40% acetone) for 30 to 45 seconds. After washing the cells 2-3 times with distilled water, an alkaline dyeing solution (Fast violet B salt) was added thereto, and the cells were cultured in a dark place at room temperature for 30 minutes. Then the cells were washed twice with distilled water, and treated with Mayer's Hematoxylin solution for 10 to 20 seconds. After removing the solution, the cells were washed with tap water and dried. The stained tissues were covered with a cover slide while using an aqueous mounting solution for observation. Because cells differentiated into osteoblasts are stained dark brown due to activation of intra-cellular alkaline phosphatase, the degree of osteogenic induction of the cells was evaluated based on the degree of staining.

<11-2> Adipogenic Induction and Fat Staining

For adipogenic induction, 500-1000 cells were placed in each well of a 6-well plate, and an adipogenic induction medium (0.5 mM 3-isobutyl-1-methyl xanthine, 0.2 mM indomethacin, 10 μM insulin, 1 μM dexamethasone/UVAB, and DMEM medium supplemented with 10% FBS and gentamicin) was provided after 2-4 days. The medium was replaced with new differentiation medium every 3 days to induce differentiation for 3-4 weeks. The differentiated cells were washed twice with PBS and then incubated in a fixation solution (10% formalin) for 10 minutes. After washing the cells 2-3 times with distilled water, a staining solution (oil red O) was added thereto, and the cells were placed at room temperature for 30 minutes. Then, the cells were washed with distilled water and treated with Mayer's Hematoxylin solution for 10 to 20 seconds. After removing the solution, the cells were washed with tap water and dried. The stained tissues were observed, covered with a cover slide while using an aqueous mounting solution. Degree of adipogenic induction was evaluated based on degree of staining (red), and presence and degree of formation of differentiated lipid vacuoles.

The experimental results are shown in FIG. 13. FIG. 13a and FIG. 13b show results of osteogenic induction and adipogenic induction, respectively. As shown in FIG. 13, superior results in osteogenic induction and adipogenic induction were obtained when the small cell group was cultured under the CMH condition. The above results suggest that combination of the small cell size and the CMH culture condition can improve the differentiation potential of umbilical cord blood-derived mesenchymal stem cells.

<11-3> Analysis of Markers

In order to analyze the immunophenotype of cell surface antigens in umbilical cord blood-derived mesenchymal stem cells, the expression of marker proteins (CD14, CD29, CD34, CD44, CD45, CD73, CD90, CD105, HLAABC, and HLADR) were examined by FACS analysis as follows.

The original cell group and the small cell group were cultured under the conventional culture condition and the CMH condition. Then, the cells were treated with trypsin and washed twice with PBS solution. The washed cells were reacted with CD14-FITC (fluorescein isothiocyanate), CD34-FITC, CD45-FITC and HLADR FITC, known negative antigens in mesenchymal stem cells, and with CD73-PE (phycoerythrin), CD90-PE, CD105-PE, and HLAABC-PE, known positive antigens strongly expressed in mesenchymal stem cells. The ratio of cells expressing the markers to the total cells was obtained by detecting signals of secondary antibodies by FACS machine. Analysis after the reaction was conducted using FACSCalibur flow cytometer (Becton Dickinson, San Jose, Calif., USA) and CELLQUEST software.

The experimental results are shown in Table 5.

TABLE 5

| Marker | CD14 | CD34 | CD45 | HLADR | CD29 | CD44 | CD90 | CD105 | HLAABC |
|---|---|---|---|---|---|---|---|---|---|
| Original cell group + Conventional culture | − | − | − | − | + | + | + | + | + |

TABLE 5-continued

| Marker | CD14 | CD34 | CD45 | HLADR | CD29 | CD44 | CD90 | CD105 | HLAABC |
|---|---|---|---|---|---|---|---|---|---|
| Small cell group + Conventional culture | − | − | − | − | + | + | + | + | + |
| Original cell group + CMH culture | − | − | − | − | + | + | + | + | + |
| Small cell group + CMH culture | − | − | − | − | + | + | + | + | + |

As shown in Table 5, there was no difference in the expressions of marker proteins in mesenchymal stem cells according to cell size or culture conditions.

The results reveal that the small cells and the CMH culture condition of the present invention does not significantly change the basic characteristics of umbilical cord blood-derived mesenchymal stem cells.

What is claimed is:

1. A method for culturing mesenchymal stem cells, comprising the steps of:
   (1) isolating mesenchymal stem cells having a size of 8 µm or less; and
   (2) culturing the isolated mesenchymal stem cells in a medium containing 2.1 to 3.8 mM of calcium and 1.0 to 3.0 mM of magnesium under a condition of 2 to 5% oxygen.

2. The method of claim 1, wherein the mesenchymal stem cells are derived from umbilical cord blood, bone marrow, lipid, muscle, skin, amniotic fluid, umbilical cord, or tooth.

3. The method of claim 1, wherein the isolation of the mesenchymal stem cells of the step (1) is performed by passing the mesenchymal stem cells through a filtration membrane having a pore size of 8 µm.

4. The method of claim 1, wherein the medium is selected from the group consisting of Dulbecco's modified eagle medium (DMEM), minimal essential medium (MEM), α-MEM, McCoys 5A medium, eagle's basal medium, Connaught Medical Research Laboratory (CMRL) medium, Glasgow MEM, Ham's F-12 medium, Iscove's modified Dulbecco's medium (IMDM), Leibovitz's L-15 medium, Roswell Park Memorial Institute (RPMI) 1640 medium, medium 199, and Hank's medium 199.

5. The method of claim 4, wherein the medium comprises 5 to 30% of fetal bovine serum.

6. The method of claim 4, wherein the medium does not comprise fetal bovine serum but a serum replacement.

7. The method of claim 1, wherein the medium is based on an α-MEM supplemented with 5 to 30% of fetal bovine serum, 0.3 to 2.0 mM of calcium, and 0.2 to 2.2 mM of magnesium.

8. The method of claim 1, wherein the cultured mesenchymal stem cells are sub-cultured under the same culture conditions as described in claim 1.

9. A method for improving proliferative capacity and differentiation potential of mesenchymal stem cells, comprising the steps of:
   (1) isolating mesenchymal stem cells having a size of 8 µm or less; and
   (2) culturing the isolated mesenchymal stem cells in a medium containing 2.1 to 3.8 mM of calcium and 1.0 to 3.0 mM of magnesium under a condition of 2 to 5% oxygen.

10. The method of claim 1, wherein the calcium concentration in the medium is 3.3 to 3.8 mM.

11. The method of claim 9, wherein the calcium concentration in the medium is 3.3 to 3.8 mM.

* * * * *